(12) United States Patent
Rabenstein et al.

(10) Patent No.: US 6,672,869 B2
(45) Date of Patent: Jan. 6, 2004

(54) PLUG CONNECTION FOR JAW STUMP MODELS

(75) Inventors: Norbert Rabenstein, Hanau (DE); Wilfried Hentschel, Florstadt (DE); Egbert Kremer, Hanau (DE); Ulrich Birkholz, Grosskrotzenburg (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/946,770

(22) Filed: Sep. 6, 2001

(65) Prior Publication Data

US 2002/0049009 A1 Apr. 25, 2002

(30) Foreign Application Priority Data

Sep. 13, 2000 (DE) .......................................... 100 45 543

(51) Int. Cl.⁷ .............................................. A61C 19/00
(52) U.S. Cl. ..................................................... 433/74
(58) Field of Search .............................. 433/74, 72, 75, 433/213, 214; 411/508, 509; 24/624, 614, 618

(56) References Cited

U.S. PATENT DOCUMENTS 3,153,283 A * 10/1964 Weissman .................... 433/176
3,787,975 A * 1/1974 Zuest ........................... 433/182

FOREIGN PATENT DOCUMENTS

| CA | 1069355 | * | 1/1980 |
| DE | 26 25 950 A1 | | 12/1977 |
| DE | 43 00 926 A2 | | 7/1994 |
| DE | 4300926 A1 | | 7/1994 |
| EP | 0 335 285 A2 | | 10/1989 |

* cited by examiner

*Primary Examiner*—Kevin Shaver
*Assistant Examiner*—Melba Bumgarner
(74) *Attorney, Agent, or Firm*—Smith, Gambrell & Russell, LLP (57) ABSTRACT

A plug connection for jaw stump models for the releasable connection of tooth crown segments or jaw segments to a model base, which includes a plug pin (1) which can be connected in snap-lock fashion with a sleeve (12). A non-rotationally symmetric design of a rotational locking section (4), and a cross pin (7) arranged perpendicular to the plug pin axis, prevent rotary movement of the plug pin (1) in the sleeve. Disposed at the end of the plug pin (1) facing the sleeve is a spring element (8), which is provided with a circumferential annular groove (11) for a snap-locking connection with the sleeve. The spring element (8) comprises two spring tongues (10) separated by a continuous longitudinal slot (9). The sleeve provided for receiving the plug pin (1) comprises a projection projecting into the inner chamber for the snap-lock connection of the plug pin (1) with the sleeve as well as a sleeve opening region matching the rotational locking section (4) of the plug pin (1).

37 Claims, 5 Drawing Sheets

PLUG CONNECTION FOR JAW STUMP MODELS

BACKGROUND OF THE INVENTION

1. Field of the Invention

The invention relates to a plug connection for jaw stump models for the releasable securing of tooth crown segments or jaw segments to a model base, with a plug pin and a sleeve.

2. Description of the Related Art

In the context of dental treatment, if it is necessary to replace one or more teeth, or possibly even the replacement of a jaw segment, then the implants provided need to be specially manufactured and adapted for the patient in each instance. For this purpose, a dental impression of the patient is often produced, which then serves as an initial mold for a jaw stump model. This jaw stump model is an identical reproduction of the patient's set of teeth. The region which is to be replaced in the patient's oral cavity by the implant, for example a tooth crown segment, is removed from the model. A prefabricated implant blank can then be adapted step by step to the model, until it obtains the shape required for the patient's treatment. The implant, which is specially prepared in this manner for the patient, can then be operatively secured in the oral cavity of the patient, without the need for complex preparation of the implant or secondary working.

For the adaptation of the implant to the jaw stump model, which precedes the surgical intervention, it is first necessary to secure the implant to the model. However, it is almost always necessary, during the course of the step by step adaptation and secondary improvement, for the implant to be removed from the model several times, and then secured to the model again. In this respect, it is necessary to ensure that the implant is secured to the jaw stump model again in exactly the same position following each interim removal. Otherwise, it would not be possible to precisely adapt the implant to the model and therefore to the patient.

For this reason, it is known to secure plug pins in the implant, by means of which the implant can be fitted into corresponding bores in the model. However, given that the model may be made of plaster, for example, there is a risk of the bores becoming damaged during each securing or removal of the implant as a result of material wear, so that precise positioning of the implant is not guaranteed on a long-term basis.

Plug connections are described, for example, in Laid-Open Specification EP 0 335 285 A2, which, in addition to a plug pin, also comprise a sleeve which is embedded in the jaw stump model. The sleeve is made of sufficiently resistant material, such as metal, and prevents possible damage to the jaw stump model by the plug pin.

Because a rotationally symmetrical plug connection of this type cannot prevent rotary movements of the implant about the pin axis, additional measures are required for reliable and reproducible securing of the implant to the jaw stump model. Thus, it is known to prevent a rotary movement of the implant by means of two plug connections fitted adjacent one another (DT 26 25 950 A1). However, this is associated with a high labor outlay, and requires a large amount of space, which is not always possible or tenable.

If the sleeve and the plug pin are not aligned exactly axially parallel in plug connections of this type, then the plug pin often tilts in the sleeve during securing and removal of the implant from the model. The resulting stresses can damage both the jaw stump model and, in particular, the securing of the plug pin in the implant, which can result in a loss of precision in the manufacture of the implant. The more plug connections used for an implant, in order, for example, to rule out rotary movements of the implant, the higher the requirements for exact alignment of the plug connections in order to prevent stresses or tilting.

In a known plug connection (DE 43 00 926 A1), the plug pin has a slightly conical design, so that sufficiently secure positive and frictional locking between the plug pin and the sleeve is only produced once the plug pin has fully penetrated the similarly conically tapering sleeve. By means of knob-like raised elements on the inside of the sleeve, made of plastics material, the retaining force of the plug pin in the sleeve can be increased. However, here, too, a secure connection of the plug pin in the sleeve is only guaranteed in the case of an exact axially parallel alignment of the two parts. In addition, in order to prevent a rotary movement of the implant, it is necessary to secure the latter to the model by means of at least two plug connections of the above type.

Ever advancing developments in dental medicine, in the use of implants, demand increasing precision in the manufacture and adaptation of the implants. As a result of the constant and high loading of a fitted implant in the oral cavity, for example during chewing, a best-possible adaptation of the implant to the respective patient is a prerequisite for a secure connection of the implant to the jaw of the patient which can withstand these stresses on a long-term basis.

It is therefore an object of the invention to design a plug connection for jaw stump models, of the generic type, so that a reliable and easily releasable securing of the implant to the model base is possible, rotary movement of the implant about the axis of the plug connection being eliminated. Furthermore, stresses and tilting of the plug pin in the sleeve are eliminated, even in cases where the two parts are not aligned exactly axially parallel.

SUMMARY OF THE INVENTION

This and other objects are achieved according to the invention, in which the plug pin is connected in a snap-locking fashion with the sleeve, and in which rotational locking prevents rotary movement of the plug pin in the sleeve.

The present invention thus relates to a plug pin, connected in a snap-lock fashion with the sleeve, whereby rotational locking prevents a rotary movement of the plug pin in the sleeve. A snap-lock connection of the plug pin and the sleeve results in a sufficiently stable securing of the implant to the model base. Consequently, the plug pin can be constructed in such a manner that it can be introduced almost fully into the sleeve with a clearance significantly facilitating handling. Only in the end position prescribed by the snap-lock connection is the plug pin fixed in a predetermined position. In order to remove the implant, it is only necessary to release the snap-lock connection between the plug pin and the sleeve. The plug pin can then be fully withdrawn from the sleeve, without thereby generating stresses or without the danger of the plug pin tilting with the sleeve. As a result of this snap-lock connection, a uniform penetration depth of the plug pin in the sleeve is automatically ensured. Only once the implant is arranged in the provided position on the model base is the snap-locking connection between the plug pin and sleeve produced.

As a result of the rotational locking, a rotary movement of the plug pin in the sleeve is ruled out. Consequently, it is possible, using a single plug connection, to prevent rotary movement of the implant secured to the model base. Additional plug connections are therefore unnecessary. In addition to resulting in a saving in labor and materials, this also means that a plug connection of this type can also be used in the case of very small implants having a small contact surface area with the model base.

The maximum penetration depth of the plug pin in the sleeve is defined by an abutment. An abutment of this type can be provided using simple means in manufacturing technology, for example by the length of the plug pin or a projection projecting radially from the plug pin. In this manner, in addition to the snap-locking connection, the maximum penetration depth of the plug pin in the sleeve can be reliably and precisely determined using little outlay.

According to an advantageous embodiment of the inventive idea, the plug pin comprises, at its end facing the sleeve, a spring element with recesses for a snap-locking connection with the sleeve. When the plug pin is introduced into the sleeve, the spring element is slightly bent by a projection projecting into the inner chamber of the sleeve, until the spring element is connected in a snap-locking manner with the projection of the sleeve in the region of the recess provided. The force necessary for the deformation of the spring element can be determined by the design and material of the spring element. In this respect, the spring element is expediently constructed in such a manner that, on the one hand, a sufficiently secure snap-locking connection of the plug pin and the sleeve is ensured, whilst on the other hand, damage to the sleeve or plug pin, or the implant associated therewith as a result of excessive stresses, is ruled out.

Advantageously, the spring element comprises a substantially cylindrical basic element, which is divided into a plurality of spring tongues by at least one continuous longitudinal slot extending as far as the end facing the sleeve. In this manner, it is possible using simple means to produce a robust spring element which is substantially independent of the alignment of the plug pin in the sleeve. Additional components fitted to the plug pin are unnecessary for a spring element of this type. By appropriately dimensioning the longitudinal slot, the force required for a deformation of the spring tongues can be prescribed as a function of the material of the plug pin.

According to one embodiment of the invention, the projection which projects into the inner chamber of the sleeve is constructed as an annular circumferential bead. In association with a corresponding recess on the spring element, it is thus possible to effect a snap-locking connection between the plug pin and the sleeve along the entire circumference. The retaining force necessary for securedly fixing the plug pin in the sleeve can be uniformly distributed over the annular circumferential bead and need not be applied locally. The snap-lock connection can thus be effected in such a manner that it is distributed over a plurality of spring tongues, so that a low bead height, and therefore a slight bending of the spring tongues during the introduction of the plug pin, is sufficient for a secure fixing of the implant to the model base.

The recess of the spring element can also be constructed as a continuous cross bore, which extends perpendicular to the pin axis and engages around a projection constructed as a locking pin projecting into the inner chamber of the sleeve. The function of the annular circumferential bead constricting the sleeve cross section can also be fulfilled by a locking pin arranged transversely in the inner chamber of the sleeve. When the plug pin is introduced into the sleeve, the individual locking tongues are not compressed, but are instead bent slightly outwards. The recess in the spring element provided for the snap-locking connection can be realized in a simple manner, in terms of manufacturing technology, as a cross bore extending through the spring element. In the end position of the plug pin, the locking pin is disposed in the region of the cross bore of the spring element, which then engages around the locking pin in a snap-locking manner. Since both the cross bore in the spring element of the plug pin, and the locking pin in the inner chamber of the sleeve, are aligned along a common axis perpendicular to the pin axis for a snap-locking connection, a specific azimuthal position of the plug pin is thereby also prescribed. Any slight twisting away from this position results in a spring force counteracting this rotary movement.

Advantageously, in the end position of the plug pin in the sleeve prescribed by the abutment, the recess of the spring element has a defined degree of offset relative to the projection which projects into the inner chamber of the sleeve, so that the plug pin is additionally fixed in the end position with a permanently acting tensile force. The spring action of the spring element generates a force which pulls the plug pin into the sleeve interior. Without the abutment defining the end position, the plug pin, as a result of this tensile force, would penetrate the sleeve to such a degree that the recess of the spring element would come to rest above the projection which projects into the inner chamber of the sleeve, and the deformation of the spring element would be minimized. It is at least necessary to overcome this permanently acting tensile force, in order to remove the plug pin from the sleeve. In this manner, accidental slight slipping of the plug pin out of the sleeve is prevented. This type of design, with the snap-lock connection between the plug pin and the sleeve, results in a precisely defined and reproducible securing position of the implant on the model base. This is true even in the case of deviations in the dimensions of the plug pin and the sleeve, which are unavoidable using current manufacturing technology, and in the case of an alignment of the two components which is not exactly axially parallel.

According to an advantageous embodiment, the plug pin comprises a substantially cylindrical basic form, with a non-rotationally symmetric rotational locking section which projects radially, at least in part, and engages in the region of the sleeve opening with a matching inner chamber of the sleeve. Only when the plug pin is almost fully introduced into the sleeve do laterally projecting, non-rotationally symmetric projections of the plug pin engage with the sleeve. In the region of the sleeve opening, the sleeve is designed in such a manner that the rotational locking section of the plug pin can only be introduced into the sleeve in a given alignment. Once the rotational locking section has been at least partially pushed into the sleeve, a rotation of the plug pin is no longer possible. In this respect, the length of the rotational locking section can be adapted to respective requirements.

According to another embodiment, the rotational locking section comprises a radially projecting, substantially cylindrical basic form, with at least one flattened section extending parallel to the plug pin axis, and in the region of the sleeve opening, the sleeve comprises a matching, inwardly projecting projection. A flattened section of this type, in the otherwise cylindrical rotational locking section, can be produced during manufacture with little outlay. A matching design of the sleeve opening only allows for a single alignment of the plug pin in the sleeve. A counter pressure of the sleeve acting upon the flattened section counteracts a rotation of the plug pin in the sleeve.

According to a further advantageous embodiment, the diameter of the spring element is, at most, only as large as the smallest internal diameter of the sleeve in the region of the sleeve opening. In this embodiment, the spring element of the plug pin can be introduced into the sleeve unimpeded and independently of the alignment of the plug pin. Already, at this stage, the implant can no longer accidentally fall from the model base. An exact alignment of the implant is considerably facilitated when the plug pin is partially introduced.

BRIEF DESCRIPTION OF THE DRAWINGS

The present invention will be further understood with reference to the accompanying drawings, wherein.

DETAILED DESCRIPTION OF THE INVENTION

Figure 1:
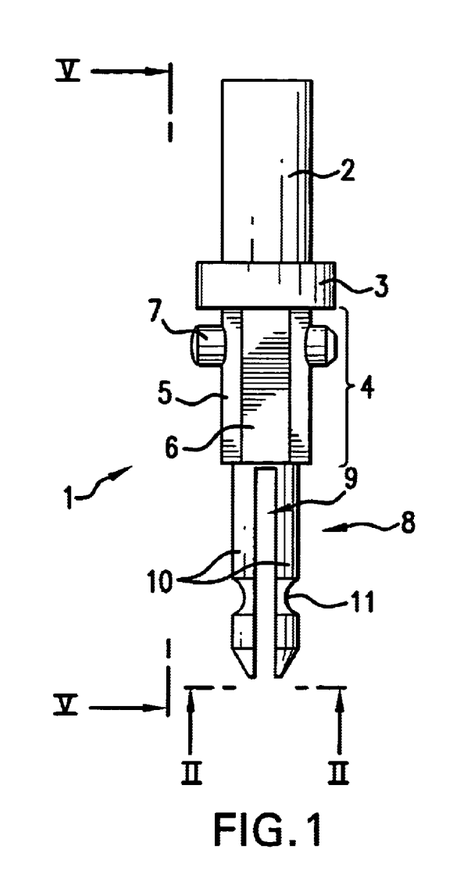
FIG. 1 is a side view of a plug pin.
Figure 2:
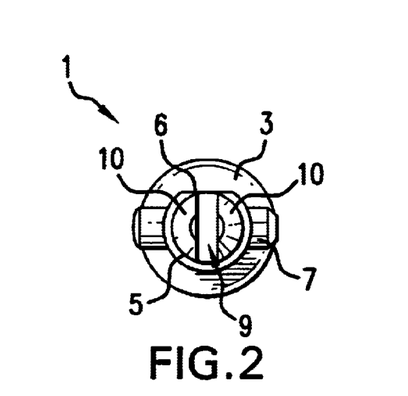
FIG. 2 is a plan view in the direction II of the plug pin illustrated in FIG. 1.

The plug pin 1 illustrated in FIGS. 1 and 2 comprises a cylindrical shaft 2, to which the implant is secured. A radially circumferential projection 3 limits the shaft 2 which can be secured in the implant and forms an abutment, which prescribes the end position of the plug pin 1 during the introduction of the plug pin 1 into an associated sleeve. Adjoining the circumferential, radial projection 3 is the rotational lock section 4. The rotational locking section 4 comprises a substantially cylindrical basic form 5 with a flattened section 6 extending parallel to the plug pin axis. In addition to the non-rotationally symmetric design of the rotational locking section 4 caused by the flattened section 6, the rotational lock section comprises a continuous cross pin 7 projecting from both sides. Disposed at the sleeve end of the plug pin 1 is a spring element 8. A continuous longitudinal slot 9 divides the substantially cylindrical spring element 8 into two spring tongues 10, each with an almost semi-circular cross section. The two spring tongues 10 are provided with a circular circumferential annular groove 11.

Figure 3:
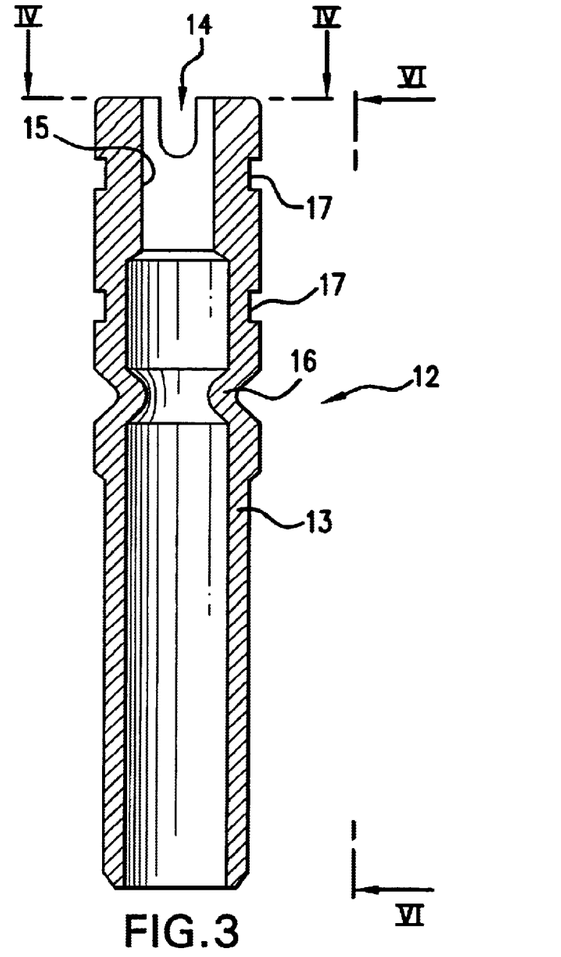
FIG. 3 is a section through a sleeve.
Figure 4:
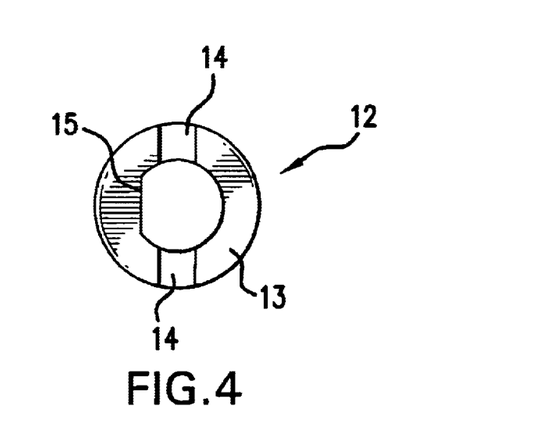
FIG. 4 is a front view in the direction IV of the sleeve illustrated in FIG. 3.

The plug pin 1 shown in FIGS. 1 and 2 is provided for use together with the sleeve 12 shown in FIGS. 3 and 4. The sleeve 12 is formed by a substantially cylindrical basic sleeve element 13. Disposed at the end of the basic sleeve element 13 receiving the plug pin 1 are two opposing, round-ended recesses 14. The latter are used for receiving the cross pin 7 projecting on both sides. The substantially cylindrical inner chamber in the region of the sleeve opening is constricted on one side by a flat projection 15 matching the flattened section 6 of the plug pin 1. In this respect, the round-ended recesses 14 and the flat projection 15 are arranged relative to one another in such a manner that the plug pin 1 can be introduced into the sleeve 12 as far as the abutment formed by the circumferential, radial projection 3.

The basic sleeve element 13 comprises an annular circumferential constriction 16. The inner chamber of the basic sleeve element 13 is constricted by the annular circumferential constriction 16 to such a degree that the two spring tongues 10 of the plug pin 1 are forced together as they are introduced into the sleeve 12. Only when the plug pin 1 is almost fully introduced into the sleeve 12 does the annular groove 11 enter the region of the constriction 16, thereby allowing for a relaxation of the two spring tongues 10. Together with the annular circumferential constriction 16 of the basic sleeve element 13, the two spring tongues 10 with the annular groove 11 form a snap-locking connection.

Disposed on the outside of the basic sleeve element 13 is a plurality of annular circumferential recesses 17. These provide adequately stable securing of the sleeve 12 in the model base of the jaw stump model.

It is also possible for the spring element 8 to comprise only a single spring tongue 10. By means of the shaping and choice of material of this single spring tongue, it can nevertheless be ensured that a sufficiently secure snap-locking connection of the plug pin 1 and the sleeve 12 is guaranteed. Similarly, a plurality of longitudinal slots, instead of only one longitudinal slot 9, can divide the spring element 8 into a correspondingly larger number of spring tongues.

Figure 5:
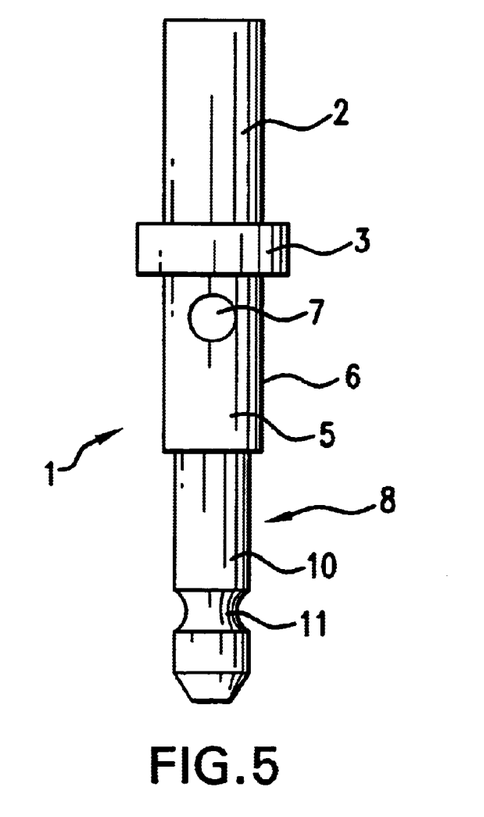
FIG. 5 is a side view in the direction V of the plug pin illustrated in FIG. 1.
Figure 6:
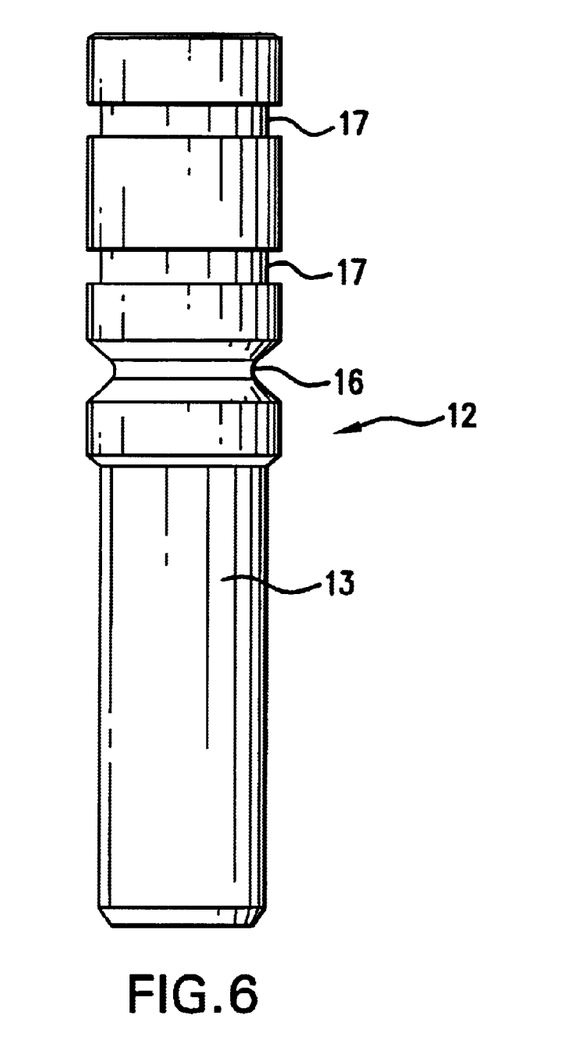
FIG. 6 is a side view in the direction VI of the sleeve illustrated in section in FIG. 4.

FIG. 5 is a side view in the direction V of the plug pin 1 illustrated in FIG. 1. The flattened section 6 and the cross pin 7 deviate visibly from the otherwise almost rotationally symmetrical construction of the plug pin 1. The side view of the sleeve 12 illustrated in FIG. 6 shows the rotationally symmetrically traced outer shape. Secure fixing of the sleeve 12 in the model base can be attained by the annular circumferential constriction 16 as well as the recesses 17.

Figure 7:
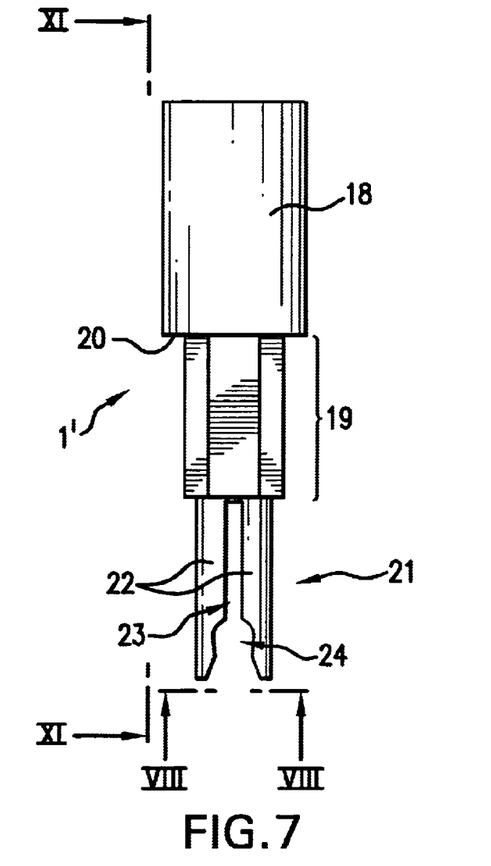
FIG. 7 is a side view of a differently designed plug pin.
Figure 8:
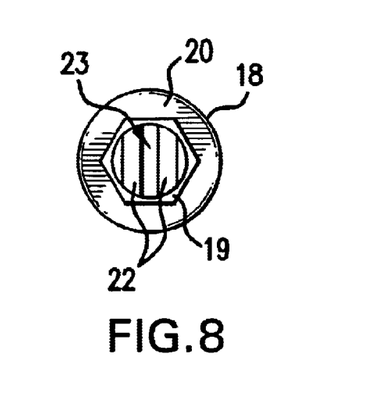
FIG. 8 is a plan view in the direction VIII of the plug pin illustrated in FIG. 7.
Figure 9:
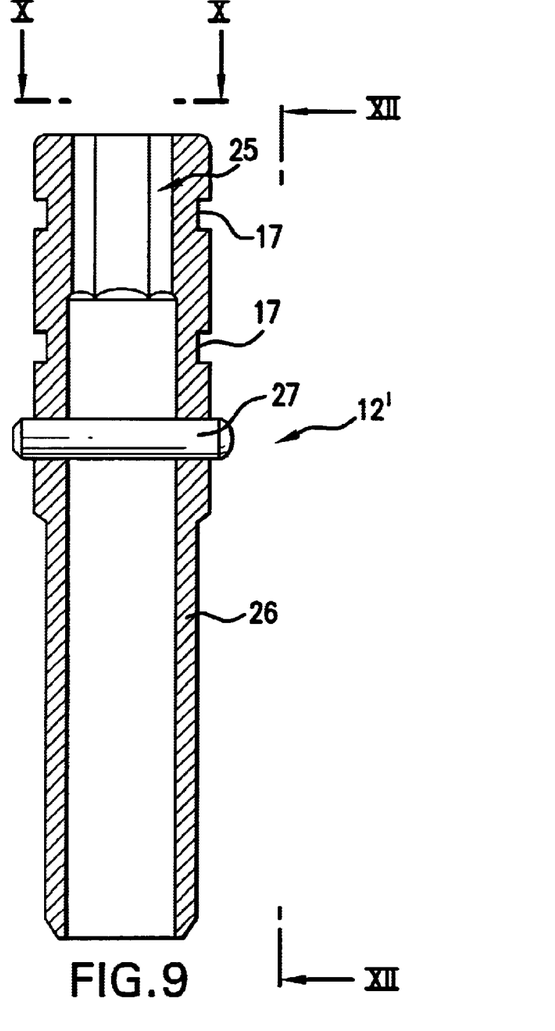
FIG. 9 is a section through a sleeve matching the plug pin shown in FIG. 7.
Figure 10:
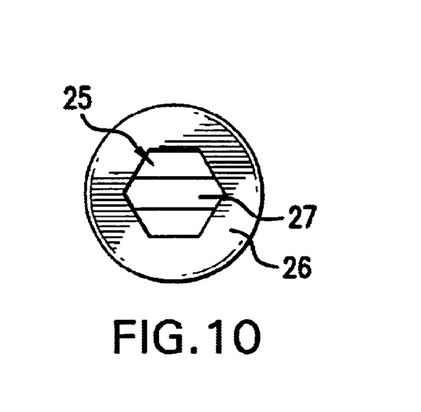
FIG. 10 is a front view in the direction X of the sleeve illustrated in FIG. 9.

Another embodiment of a plug pin 1' is illustrated in FIGS. 7 and 8. Adjoining the cylindrical shaft 18 is a rotational locking section 19 with a hexagonal cross sectional surface. As a result of the larger diameter of the shaft 18 as compared with the rotational locking section 19, the circumferential end face 20 of the shaft 18 forms an abutment, which prevents further penetration of the plug pin 1' into a matching sleeve. Arranged after the rotational locking section 19 is the spring element 21, which comprises two spring tongues 22 as in the plug pin 1 shown in FIG. 1, the spring tongues being separated from one another by a continuous longitudinal slot 23. Instead of a circumferential annular groove, the spring element 21 comprises a continuous cross bore 24. A sleeve 12' (FIGS. 9 and 10) matching the plug pin 1' comprises a sleeve opening region 25, which is adapted to the rotational locking section 19 of the plug pin 1' and also has a hexagonal cross section. However, instead of an annular circumferential constriction, the basic sleeve element 26 of the sleeve 12' comprises a continuous locking pin 27 arranged perpendicular to the sleeve axis. When the plug pin 1' is introduced into the sleeve 12', the two spring tongues 22 are bent slightly apart in the region of the locking pin 27, until the locking pin 27 comes to rest in the continuous cross bore 24 of the spring element 21. The two spring tongues 22 thereby enclose the locking pin 27, so that a snap-locking connection of the plug pin 1' and the sleeve 12' is produced.

As a result of the small diameter of the spring element 21, it is possible to introduce the plug pin 1' into the sleeve 12', in any manner, as far as the rotational locking section 19. The hexagonal cross sectional surface both of the rotational locking section 19 and of the sleeve opening region 25 matching the rotational locking section requires a defined alignment of the plug pin 1' relative to the sleeve 12'. The locking pin 27 needs to be arranged in such a manner that it is possible for the spring tongues 22 to engage around the locking pin 27 in an alignment of the plug pin 1' prescribed by the rotational locking section 19.

Figures 11, 12:
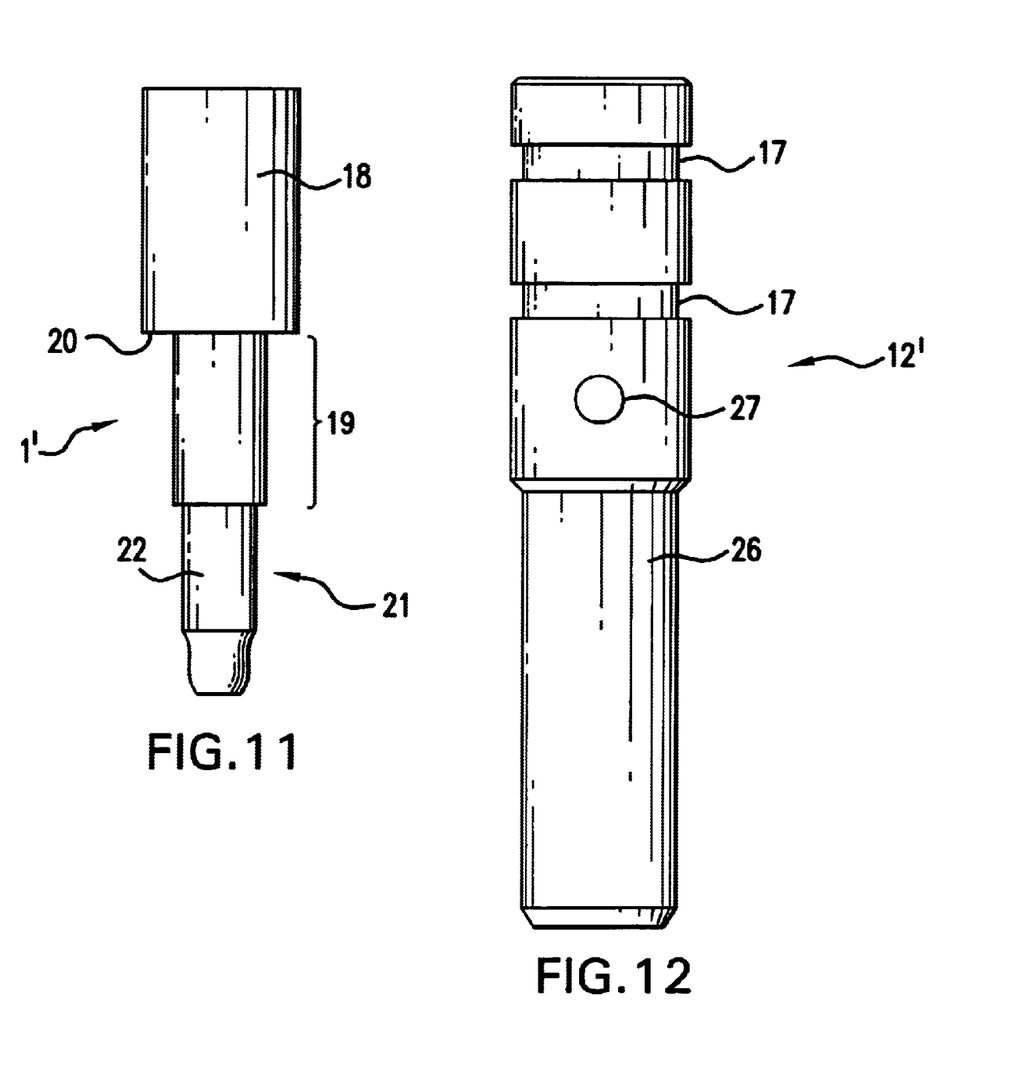
FIG. 11 is a side view in the direction XI of the plug pin illustrated in FIG. 7.
FIG. 12 is a side view in the direction XII of the sleeve illustrated in FIG. 9.

A side view of the plug pin 1' and of the sleeve 12' is illustrated in FIGS. 11 and 12.

Figure 13:
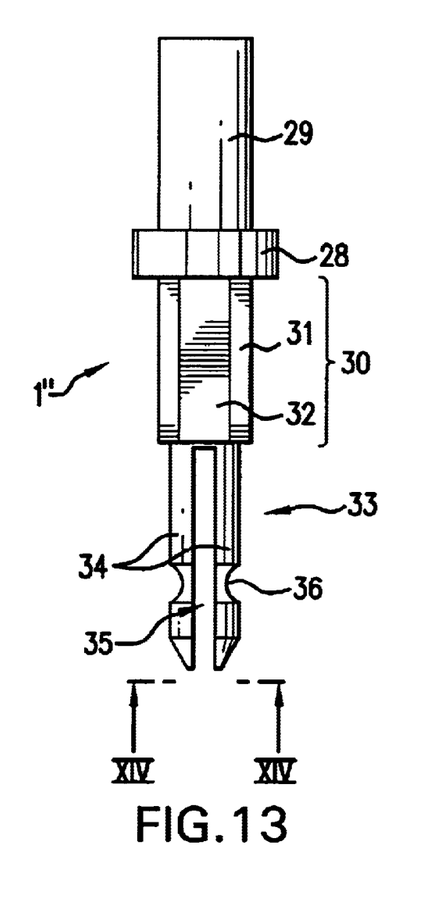
FIG. 13 is a side view of a further differently designed plug pin.
Figure 14:
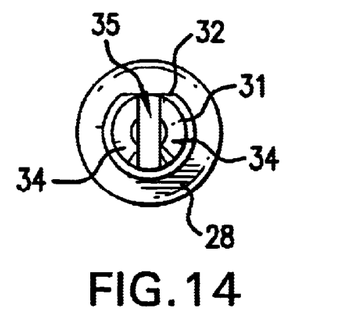
FIG. 14 is a plan view in the direction XIV of the plug pin illustrated in FIG. 13.

A plug pin 1" illustrated in FIGS. 13 and 14 comprises an advantageous combination of individual design features of the two plug pins 1 and 1' shown in FIGS. 1 and 7. A radial circumferential projection 28 divides the shaft 29 provided for the securing in the implant from the region of the plug pin 1" which is to be introduced into a sleeve. A rotational locking section 30 comprises a substantially cylindrical basic form 31, on which a flattened section 32 is disposed. A spring element 33 is formed by two spring tongues 34, which are separated from one another by a continuous longitudinal slot 35. The spring element 33 comprises a circumferential annular groove 36.

Figure 15:
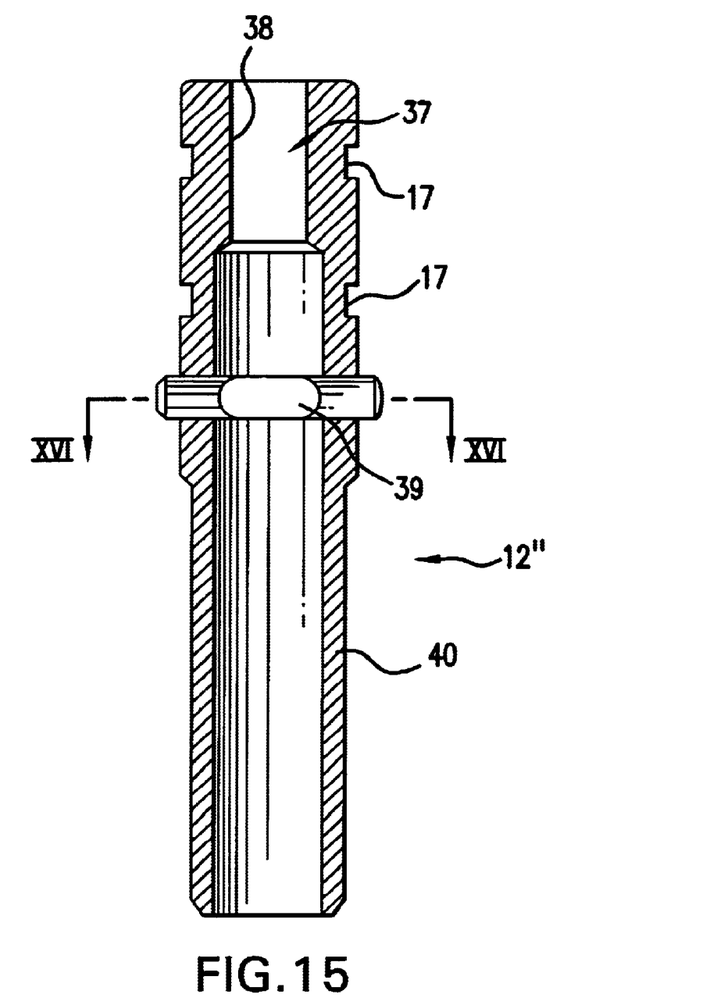
FIG. 15 is a section through a sleeve matching the plug pin illustrated in FIG. 13.
Figure 16:
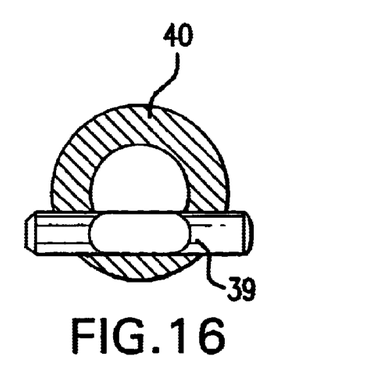
FIG. 16 is a section taken along line XVI—XVI of the sleeve illustrated in FIG. 15.

A sleeve 12" provided for the connection with the plug pin 1" consequently has an almost cylindrical sleeve opening region 37, which comprises a flat projection 38 on one side. Instead of an annular circumferential constriction, a laterally offset locking pin 39 is arranged at this location. The latter only partially penetrates the inner chamber of the basic sleeve element 40. When the plug pin 1" is introduced into the sleeve 12", the spring tongue 34 disposed on the same side as the locking pin 39 is bent by the locking pin. Only once the plug pin 1" has been introduced into the sleeve 12" as far as the abutment formed by the circumferential radial projection 28, does the annular groove 36 lie in the region of the locking pin 39. In its relaxed state, the spring tongue 34 enclosing the locking pin 39 forms a snap-locking connection between the plug pin 1" and the sleeve 12".

The plug pins 1, 1', 1" and the sleeves 12, 12', 12" can be integrally made of metal, ceramic material or plastics material. However, for special applications a multi-part construction may be advantageous, which is composed of different materials.

Further variations and modifications of the foregoing description will be apparent to those skilled in the art, and are intended to be encompassed by the claims which follow.

German priority application number 100 45 543.3 is relied on and incorporated herein by reference in its entirety.

We claim:

1. A plug connection, for releasably securing a model to a model base, comprising:
a plug pin, connectable in snap-lock fashion to a sleeve, provided with means for preventing rotary movement of the plug pin in the sleeve; and
the sleeve, which accepts the plug pin in a connectable, snap-lock fashion so as to prevent rotary movement of the plug pin in the sleeve;
wherein the plug pin has at a first end not facing the sleeve a cylindrical shaft for securing an implant, said cylindrical shaft being provided with an abutment which limits a maximum penetration depth of the plug pin in the sleeve; and
further wherein the plug pin is provided, at a second end of the plug pin facing the sleeve, with a spring element having at least one recess for a snap-lock connection with the sleeve, the spring element comprising at least one spring tongue.

2. The plug connection according to claim 1, wherein the spring element comprises a substantially cylindrical base element, which is divided into a plurality of spring tongues by at least one longitudinal slot.

3. The plug connection according to claim 1, wherein the spring element is provided with a circumferential, annular groove for connecting in snap-lock fashion with a matching projection of an inner chamber of the sleeve.

4. The plug connection according to claim 3, wherein the matching projection comprises an annular circumferential constriction.

5. The plug connection according to claim 1, wherein:
the recess of the spring element has a defined degree of offset relative to a projection projecting into an inner chamber of the sleeve, so that the plug pin is fixed with a permanent tensile force.

6. The plug connection according to claim 1, wherein the means for preventing rotary movement of the plug pin in the sleeve comprises a substantially cylindrical base forming a rotationally asymmetric locking section, which projects radially in part and engages in a region of a sleeve opening having a matching inner chamber of the sleeve.

7. The plug connection according to claim 6, wherein the rotational locking section comprises a radially projecting, substantially cylindrical base form with at least one flattened section extending parallel to the plug pin axis, and wherein a sleeve opening of the sleeve comprises a matching, inwardly projecting projection.

8. The plug connection according to claim 6, wherein the rotational locking section exhibits a polygonal cross sectional opening, and wherein the sleeve comprises a matching inner chamber in the sleeve opening.

9. The plug connection according to claim 1, wherein a diameter of the spring element is no larger than an internal diameter of a sleeve opening.

10. The plug connection according to claim 1, wherein the plug pin and the sleeve comprise at least one member selected from the group consisting of a metal, a ceramic material and a plastics material.

11. A plug connection, for releasably securing a model to a model base, comprising:
a plug pin, including:
a cylindrical shaft, and
a first rotationally asymmetric locking section adjacent the cylindrical shaft of the plug pin; and
a sleeve, defining an opening which accepts the plug pin in connectable, snap-lock fashion, which opening is provided with a second rotationally asymmetric locking section corresponding to that of the first rotationally asymmetric locking section, so as to prevent rotary movement of the plug pin in the sleeve;
further wherein the plug pin is provided, at an end of the plug pin facing the sleeve, with a spring element having at least one recess for a snap-lock connection with the sleeve, the spring element further comprising at least one spring tongue.

12. The plug connection according to claim 11, wherein a maximum penetration depth of the plug pin in the sleeve is limited by an abutment provided on the cylindrical shaft of the plug pin.

13. The plug connection according to claim 11, wherein the spring element is provided with a circumferential, annular groove for connecting in snap-lock fashion with a matching projection of an inner chamber of the sleeve.

14. The plug connection according to claim 13, wherein the matching projection comprises an annular circumferential constriction.

15. The plug connection according to claim 11, wherein:
a maximum penetration depth of the plug pin in the sleeve is limited by an abutment provided on the cylindrical shaft of the plug pin; and,
the recess of the spring element has a defined degree of offset relative to a projection projecting into an inner chamber of the sleeve, so that the plug pin is fixed with a permanent tensile force.

16. The plug connection according to claim 15, wherein the rotationally asymmetric locking section comprises a substantially cylindrical base form having at least one flattened section extending parallel to an axis of the plug pin.

17. The plug connection according to claim 15, wherein the rotationally asymmetric locking section exhibits a polygonal cross sectional opening.

18. The plug connection according to claim 11, wherein the plug pin and the sleeve comprise at least one member selected from the group consisting of a metal, a ceramic material and a plastics material.

19. A plug connection, comprising:
a plug pin, including:
a cylindrical shaft,
a rotational locking section, adjacent the cylindrical shaft, provided with a flattened section extending parallel to an axis of the plug pin, and
a spring element, adjacent the rotational locking section, provided with at least one spring tongue having a circumferential annular groove; and
a sleeve, defining an opening which accepts the plug pin, which opening is provided on a side of the opening with a flat projection which matches the flattened section of the rotational locking section of the plug pin, the sleeve being provided with an annular circumferential constriction which accepts the circumferential annular groove of the spring tongue to form a snap-lock connection.

20. The plug connection according to claim 19, wherein the spring element is provided with at least one continuous longitudinal slot which defines at least two spring tongues.

21. The plug connection according to claim 19, wherein a maximum penetration depth of the plug pin in the sleeve is limited by an abutment provided on the cylindrical shaft of the plug pin.

22. The plug connection according to claim 19, wherein:
a maximum penetration depth of the plug pin in the sleeve is limited by an abutment; and
the annular groove of the spring tongue has a defined degree of offset relative to the annular circumferential constriction of the sleeve, so that the plug pin is fixed with a permanent tensile force.

23. The plug connection according to claim 19, wherein the the plug pin and the sleeve each comprise at least one member selected from the group consisting of a metal, a ceramic material and a plastics material.

24. A plug connection, comprising:
a plug pin, including:
a cylindrical shaft,
a rotational locking section, adjacent the cylindrical shaft, having a polygonal cross-section, and
a spring element, adjacent the rotational locking section, which includes: a) a continuous longitudinal slot which defines at least two spring tongues, and b) a continuous cross bore; and
a sleeve, defining an opening which accepts the plug pin, which opening is provided with a polygonal cross-section which matches the polygonal cross-section of the rotational locking section of the plug pin, the sleeve being provided with a continous locking pin, arranged perpendicularly to an axis of the sleeve, which engages the continuous cross bore of the spring tongue to form a snap-lock connection.

25. The plug connection according to claim 24, wherein a maximum penetration depth of the plug pin in the sleeve is limited by an abutment provided on the cylindrical shaft of the plug pin.

26. The plug connection according to claim 24, wherein the the plug pin and the sleeve each comprise at least one member selected from the group consisting of a metal, a ceramic material and a plastics material.

27. A plug connection, comprising:
a plug pin, including:
a cylindrical shaft,
a rotational locking section, adjacent the cylindrical shaft, provided with a flattened section extending parallel to an axis of the plug pin, and
a spring element, adjacent the rotational locking section, provided with at least one continuous longitudinal slot which defines at least two spring tongues having circumferential annular grooves; and
a sleeve, defining an opening which accepts the plug pin, which opening is provided on a side of the opening with a flat projection which matches the flattened section of the rotational locking section of the plug pin, the sleeve being provided with a laterally offset locking pin which partially penetrates an inner chamber of the sleeve, and which accepts the circumferential annular groove of one of the spring tongues to form a snap-lock connection.

28. The plug connection according to claim 27, wherein a maximum penetration depth of the plug pin in the sleeve is limited by a radial circumferential projection which divides the shaft from the rotational locking section.

29. The plug connection according to claim 27, wherein the the plug pin and the sleeve each comprise at least one member selected from the group consisting of a metal, a ceramic material and a plastics material.

30. A plug connection, for releasably securing a model to a model base, comprising:
a plug pin, connectable in snap-lock fashion to a sleeve, provided with means for preventing rotary movement of the plug pin in the sleeve; and
the sleeve, which accepts the plug pin in a connectable, snap-lock fashion so as to prevent rotary movement of the plug pin in the sleeve,
wherein the plug pin is provided, at an end of the plug pin facing the sleeve, with a spring element having at least one recess for a snap-lock connection with the sleeve, the spring element being provided with a circumferential, annular groove for connecting in snap-lock fashion with a matching projection of an inner chamber of the sleeve, the matching projection comprising a laterally offset locking pin which projects into the inner chamber of the sleeve.

31. A plug connection, for releasably securing a model to a model base, comprising:
a plug pin, including:
a cylindrical shaft, and
a first rotationally asymmetric locking section adjacent the cylindrical shaft of the plug pin; and
a sleeve, defining an opening which accepts the plug pin in connectable, snap-lock fashion, which opening is provided with a second rotationally asymmetric locking section corresponding to that of the first rotationally asymmetric locking section, so as to prevent rotary movement of the plug pin in the sleeve,
wherein the plug pin is provided, at an end of the plug pin facing the sleeve, with a spring element having at least one recess for a snap-lock connection with the sleeve, the spring element comprising a substantially cylindrical base element which is divided into a plurality of spring tongues by at least one longitudinal slot.

32. A plug connection, for releasably securing a model to a model base, comprising:
a plug pin, including:
a cylindrical shaft, and
a first rotationally asymmetric locking section adjacent the cylindrical shaft of the plug pin; and
a sleeve, defining an opening which accepts the plug pin in connectable, snap-lock fashion, which opening is provided with a second rotationally asymmetric locking section corresponding to that of the first rotationally asymmetric locking section, so as to prevent rotary movement of the plug pin in the sleeve,
wherein the plug pin is provided, at an end of the plug pin facing the sleeve, with a spring element having at least one recess for a snap-lock connection with the sleeve, the spring element being provided with a circumferential, annular groove for connecting in snap-lock fashion with a matching projection of an inner chamber of the sleeve, the matching projection comprises a laterally offset locking pin which projects into the inner chamber of the sleeve.

33. A plug connection, for releasably securing a model to a model base, comprising:
a plug pin, including:
a cylindrical shaft, and
a first rotationally asymmetric locking section adjacent the cylindrical shaft of the plug pin; and
a sleeve, defining an opening which accepts the plug pin in connectable, snap-lock fashion, which opening is provided with a sleeve rotationally asymmetric locking section corresponding to that of the first rotationally asymmetric locking section, so as to prevent rotary movement of the plug pin in the sleeve, the rotationally asymmetric locking section being provided with at least one radially projecting cross pin which engages at least one matching recess of the sleeve, in the sleeve opening,
wherein a maximum penetration depth of the plug pin in the sleeve is limited by an abutment; and the plug pin is provided, at an end of the plug pin facing the sleeve, with a spring element having at least one recess for a snap-lock connection with the sleeve, the recess of the spring element having a defined degree of offset relative to a projection projecting into an inner chamber of the sleeve, so that the plug pin is fixed with a permanent tensile force.

34. A plug connection, for releasably securing a model to a model base, comprising:
a plug pin, connectable in snap-lock fashion to a sleeve, provided with means for preventing rotary movement of the plug pin in the sleeve; and
the sleeve, which accepts the plug pin in a connectable, snap-lock fashion so as to prevent rotary movement of the plug pin in the sleeve;
wherein the plug pin is provided, at an end of the plug pin facing the sleeve, with a spring element having at least one recess for a snap-lock connection with the sleeve, the recess of the spring element comprising a continuous cross bore which extends perpendicularly through an axis of the plug pin and engages in snap-lock fashion a projection comprising a locking pin which projects in an inner chamber of the sleeve.

35. A plug connection, for releasably securing a model to a model base, comprising:
a plug pin, connectable in snap-lock fashion to a sleeve, provided with means for preventing rotary movement of the plug pin in the sleeve; and
the sleeve, which accepts the plug pin in a connectable, snap-lock fashion so as to prevent rotary movement of the plug pin in the sleeve;
wherein the means for preventing rotary movement of the plug pin in the sleeve comprises a substantially cylindrical base forming a rotationally asymmetric locking section, which projects radially in part and engages in a region of a sleeve opening having a matching inner chamber of the sleeve, the rotational locking section comprising at least one radially projecting cross pin which engages at least one matching recess of the sleeve, in the sleeve opening.

36. A plug connection, for releasably securing a model to a model base, comprising:
a plug pin, including:
a cylindrical shaft, and
a first rotationally asymmetric locking section adjacent the cylindrical shaft of the plug pin; and
a sleeve, defining an opening which accepts the plug pin in connectable, snap-lock fashion, which opening is provided with a second rotationally asymmetric locking section corresponding to that of the first rotationally asymmetric locking section, so as to prevent rotary movement of the plug pin in the sleeve;
wherein the plug pin is provided, at an end of the plug pin facing the sleeve, with a spring element having at least one recess for a snap-lock connection with the sleeve; the recess of the spring element comprising a continuous cross bore, which extends perpendicularly through an axis of the plug pin, and engages in snap-lock fashion a projection comprising a locking pin which projects into an inner chamber of the sleeve.

37. A plug connection, comprising:
a plug pin, including:
a cylindrical shaft,
a rotational locking section adjacent the cylindrical shaft, provided with a flattened section extending parallel to an axis of the plug pin, and
a spring element, adjacent the rotational locking section, provided with at least one spring tongue having a circumferential annular groove; and a sleeve, defining an opening which accepts the plug pin, which opening is provided on a side of the opening with a flat projection which matches the flattened section of the rotational locking section of the plug pin, the sleeve being provided with an annular circumferential constriction which accepts the circumferential annular groove of the spring tongue to form a snap-lock connection;

wherein the rotational locking section of the plug pin is provided with a cross pin which projects from two opposing sides of the rotational locking section; and wherein the sleeve opening is provided with two opposing round-ended recesses which receive the two ends of the cross pin of the rotational locking section.

\* \* \* \* \*